United States Patent
Li et al.

(10) Patent No.: US 11,311,201 B2
(45) Date of Patent: Apr. 26, 2022

(54) FEATURE SELECTION FOR CARDIAC ARRHYTHMIA CLASSIFICATION AND SCREENING

(71) Applicant: Samsung Electronics Co., Ltd., Suwon-si (KR)

(72) Inventors: Yelei Li, San Jose, CA (US); Xin Sui, New York, CA (US)

(73) Assignee: Samsung Electronics Co., Ltd.

( * ) Notice: Subject to any disclaimer, the term of this patent is extended or adjusted under 35 U.S.C. 154(b) by 205 days.

(21) Appl. No.: 16/672,176

(22) Filed: Nov. 1, 2019

(65) Prior Publication Data
US 2020/0138306 A1    May 7, 2020

Related U.S. Application Data

(60) Provisional application No. 62/756,357, filed on Nov. 6, 2018, provisional application No. 62/755,352, filed on Nov. 2, 2018.

(51) Int. Cl.
*A61B 5/024*        (2006.01)
*G16H 50/20*        (2018.01)
(Continued)

(52) U.S. Cl.
CPC .......... *A61B 5/02405* (2013.01); *A61B 5/316* (2021.01); *A61B 5/363* (2021.01);
(Continued)

(58) Field of Classification Search
CPC ..... A61B 5/02405; A61B 5/316; A61B 5/363; A61B 5/7257; A61B 5/7264;
(Continued)

(56) References Cited

U.S. PATENT DOCUMENTS

2008/0125666 A1* 5/2008 Crozier .............. G06K 9/00496
                                                                600/509
2009/0112110 A1* 4/2009 Zhang .................... A61B 5/361
                                                                600/518
(Continued)

FOREIGN PATENT DOCUMENTS

WO    2018146690 A1    8/2018
WO    2018152635 A1    8/2018

*Primary Examiner* — Brian T Gedeon
*Assistant Examiner* — Joshua Andrew Schum-Houck
(74) *Attorney, Agent, or Firm* — Innovation Counsel LLP

(57) ABSTRACT

A method of measuring biological signals of a person including obtaining physiological signals; converting the physiological signals to an energy entropy signal, determining one or more statistical features based on the energy entropy signal, and selecting and combining two or more of the features. The features include two or more of: Shannon entropy of power spectral density (PSD) of energy entropy; minimum envelopes of three axis signals; minimum Shannon entropy of PSD of three axis entropies; standard deviation of interbeat intervals (IBIs); differences of median filtered IBIs; determinism of recurrence plot of energy entropy; Kurtosis of energy entropy; minimum peak-to-peak amplitude three axis signals; peak-to-peak amplitude of energy entropy; laminarity of recurrence plot of energy entropy; Shannon entropy of horizontal structures in recurrence plot of energy entropy; standard deviation of time-averaged spectrogram; minimum standard deviation of peak positions in spectrogram; and minimum standard deviation of peak widths in spectrogram.

20 Claims, 15 Drawing Sheets

(51) Int. Cl.
  *A61B 5/00* (2006.01)
  *A61B 5/316* (2021.01)
  *A61B 5/363* (2021.01)

(52) U.S. Cl.
  CPC .......... *A61B 5/7257* (2013.01); *A61B 5/7264* (2013.01); *G16H 50/20* (2018.01)

(58) Field of Classification Search
  CPC ............ A61B 5/02055; A61B 5/02416; A61B 5/7267; A61B 5/681; A61B 5/1102; G16H 50/20
  See application file for complete search history.

(56) References Cited

U.S. PATENT DOCUMENTS

| | | | |
|---|---|---|---|
| 2009/0209875 A1* | 8/2009 | Giorgis | A61B 5/02405 600/512 |
| 2012/0123232 A1 | 5/2012 | Najarian et al. | |
| 2012/0197831 A1* | 8/2012 | Dong | G06K 9/00516 706/20 |
| 2013/0197375 A1* | 8/2013 | Heise | A61B 5/6892 600/484 |
| 2015/0238151 A1 | 8/2015 | Sitzman et al. | |
| 2015/0374300 A1 | 12/2015 | Najarian et al. | |
| 2016/0270718 A1* | 9/2016 | Heneghan | A61B 5/0533 |
| 2016/0357886 A1* | 12/2016 | Fralick | G06F 9/453 |
| 2017/0265768 A1 | 9/2017 | Bayasi et al. | |
| 2017/0273635 A1* | 9/2017 | Li | A61B 5/7207 |
| 2018/0146922 A1 | 5/2018 | Wang et al. | |

* cited by examiner

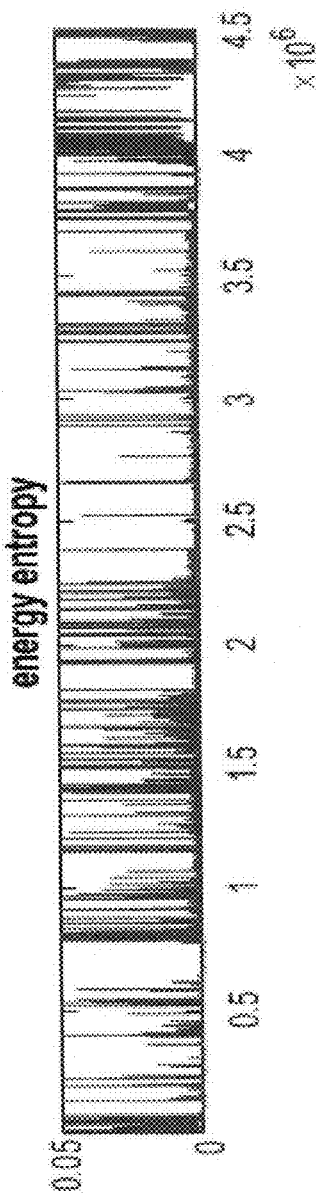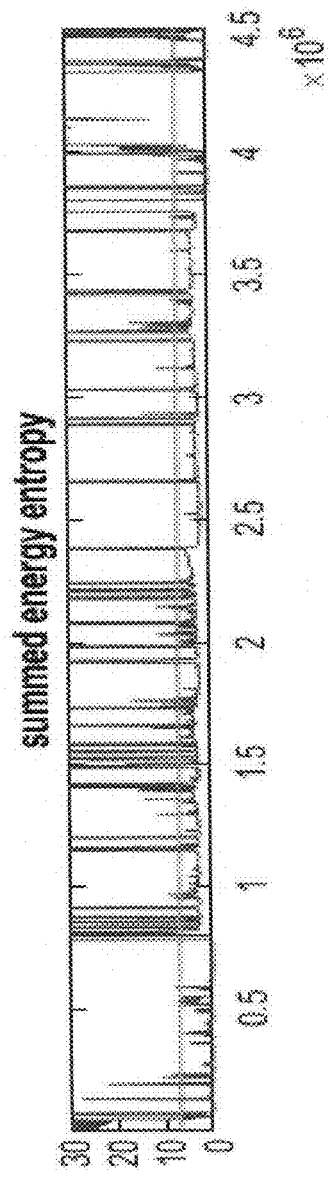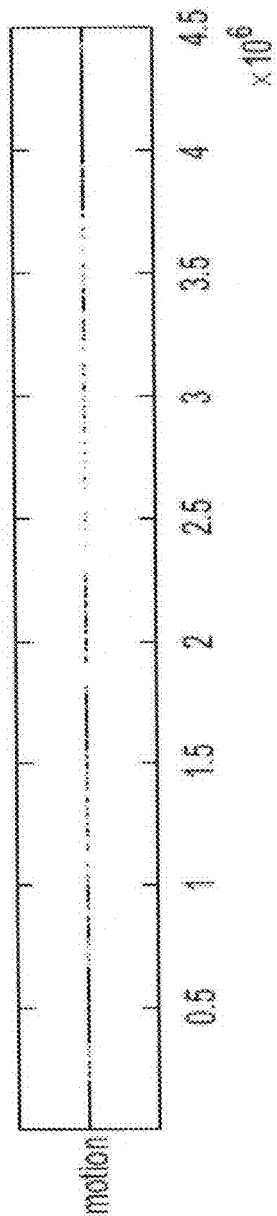
FIG. 3A
FIG. 3B
FIG. 3C

FEATURE SELECTION FOR CARDIAC ARRHYTHMIA CLASSIFICATION AND SCREENING

CROSS-REFERENCE TO RELATED APPLICATIONS

This application claims the benefit of U.S. Provisional Patent Application No. 62/755,352 filed on Nov. 2, 2018 and U.S. Provisional Patent Application No. 62/756,357 filed on Nov. 6, 2018, the contents of which are incorporated herein by reference.

BACKGROUND

The inventive concept disclosed herein relates to a method and apparatus for detecting cardiac arrhythmia.

Cardiac arrhythmia is a group of conditions in which the heartbeat is irregular, too fast, or too slow. While most types of arrhythmia are not serious, this condition can predispose a person to complications such as stroke or heart failure, and may be a risk factor for cardiac arrest. Arrhythmia affects millions of people. In Europe and North America alone, a type of arrhythmia called atrial fibrillation (AFib) may affect almost 3% of the population, and may be the cause of hundreds of thousands of deaths per year.

Cardiac arrhythmia detection typically involves collecting physical signals from a person and processing the signals. Signal processing typically manipulates large amounts of numeric data, and may include processes such as sorting, formatting, aggregation, classification, validation, and reporting.

Cardiovascular periodicity generally refers to the nearly regular, recurrent blood pressure and volume pulses induced by the heart. The time length of each period between consecutive individual heart beats is commonly referred to as the interbeat interval (IBI). The heart rate is the inverse of the cardiovascular periodicity. During normal heart functioning, there is some variation in the continuous time series of IBI values. This natural variation is known as heart rate variability (HRV). Relatively noisy or low-amplitude sensor signals may add measurement error that further detracts from the nearly periodic nature of the observed heart beat signal. Thus, the observed heart beat sensor signal typically represents a quasiperiodic function. That is, the signal is similar to a periodic function but displays irregular periodicity and does not meet the strict definition of a periodic function that recurs at regular intervals. Quasiperiodic behavior includes a pattern of recurrence with a component of unpredictability that does not lend itself to precise measurement.

The time intervals between consecutive heart beats are customarily measured in an electrocardiogram (ECG or EKG) from the initiation of each of two consecutive QRS complexes, corresponding to the contraction of the heart ventricles, each of which typically includes three component waveforms (the Q-wave, R-wave and S-wave). However, the initiation of the QRS complex may be difficult to locate in relatively noisy or low-amplitude sensor signals, which may lead to measurement error. Thus, IBI is sometimes measured between R-wave peaks in consecutive heart beats to reduce measurement error.

IBI may also be determined from a peripheral pulse measurement, such as a digital volume pulse measurement, e.g., photoplethysmogram (PPG), an optically obtained plethysmogram, or volumetric measurement of an organ. PPG sensors have been used to monitor respiration and heart rates, blood oxygen saturation, hypovolemia, and other circulatory conditions.

Currently, diagnosis for arrhythmia commonly involves electrocardiogram (ECG) or halter monitor. However, there is much room for signals to be misinterpreted due to ambiguity and lack of clarity. A clearer and more accurate way to classify and screen for the exact type of arrhythmia is desired.

SUMMARY

In one aspect, this disclosure presents a method of measuring biological signals of a person by obtaining, via one or more sensors, physiological signals of the person, and via a processor, converting the BCG signals to an energy entropy signal, determining one or more statistical features based on the energy entropy signal, and selecting and combining two or more of the statistical features. The statistical features include two or more of the following:
  Shannon entropy of power spectral density (PSD) of energy entropy;
  minimum envelopes of x-, y-, and z-axis signals;
  minimum Shannon entropy of PSD of x-, y-, and z-axis entropies;
  standard deviation of interbeat intervals (IBIs);
  differences of median filtered IBIs;
  determinism of recurrence plot of energy entropy;
  Kurtosis of energy entropy;
  minimum peak-to-peak amplitude of x-, y-, and z-axis signals;
  peak-to-peak amplitude of energy entropy;
  laminarity of recurrence plot of energy entropy;
  Shannon entropy of horizontal structures in recurrence plot of energy entropy;
  standard deviation of time-averaged spectrogram;
  minimum standard deviation of peak positions in spectrogram; and
minimum standard deviation of peak widths in spectrogram.

In another aspect, the disclosure pertains to a system for measuring biological signals of a person. The system includes a sensor module that acquires physiological signals of the person, a pre-processing module that converts the physiological signals to an energy entropy signal, a feature extraction module that determines one or more statistical features based on the energy entropy signal, and a feature selection module that selects and combines two or more of the statistical features.

In yet another aspect, the disclosure pertains to a non-transitory computer-readable storage medium storing instructions for measuring biological signals of a person, the instructions being instructions to execute the above-described method.

The method and apparatus of the disclosure allow a more accurate arrhythmia detection than the conventionally-available methods.

BRIEF DESCRIPTION OF THE DRAWINGS

FIG. 3A depicts an energy entropy calculated from a tri-axial signal;

FIG. 3B depicts the summed energy entropy of patients;

FIG. 3C depicts motion annotated based on the plot of FIG. 3B;

DETAILED DESCRIPTION

A generic feature selection for cardiac arrhythmia classification and screening framework on various physiological signals is presented. The physiological signals are processed to extract features, for example using frequency analysis, temporal analysis, time frequency analysis, recurrent analysis and cardiac rhythm analysis. In this disclosure, the features are preprocessed, extracted, and selectively combined to build an accurate model for cardiac arrhythmia classification.

Although examples will be described in terms of five features (frequency analysis, temporal analysis, time frequency analysis, recurrent analysis, and cardiac rhythm analysis), other features may be used and not all the features need to be used together. The disclosure uses ballistocardiogram (BCG) signals as an example of physiological signals that may be used for the inventive concept. However, this is for clarity of illustration and does not limit the inventive concept to being used only with BCG signals. The inventive concept is adaptable to being used with other physiological signals with or without modification. BCG signals, if used, may be used alone or in conjunction with other physiological signals.

Physiological signals such as electrocardiogram (ECG), photoplethysmogram (PPG), ballistocardiogram (BCG), and semismocardiogram (SCG), may be collected as raw data. The raw data are then preprocessed to obtain an envelope signal. The envelope signal, now the raw signals, is used for feature extraction. The features are then selectively combined to show the desired information most accurately and clearly, leading to more accurate labeling of what is happening with the person.

Figure 1:
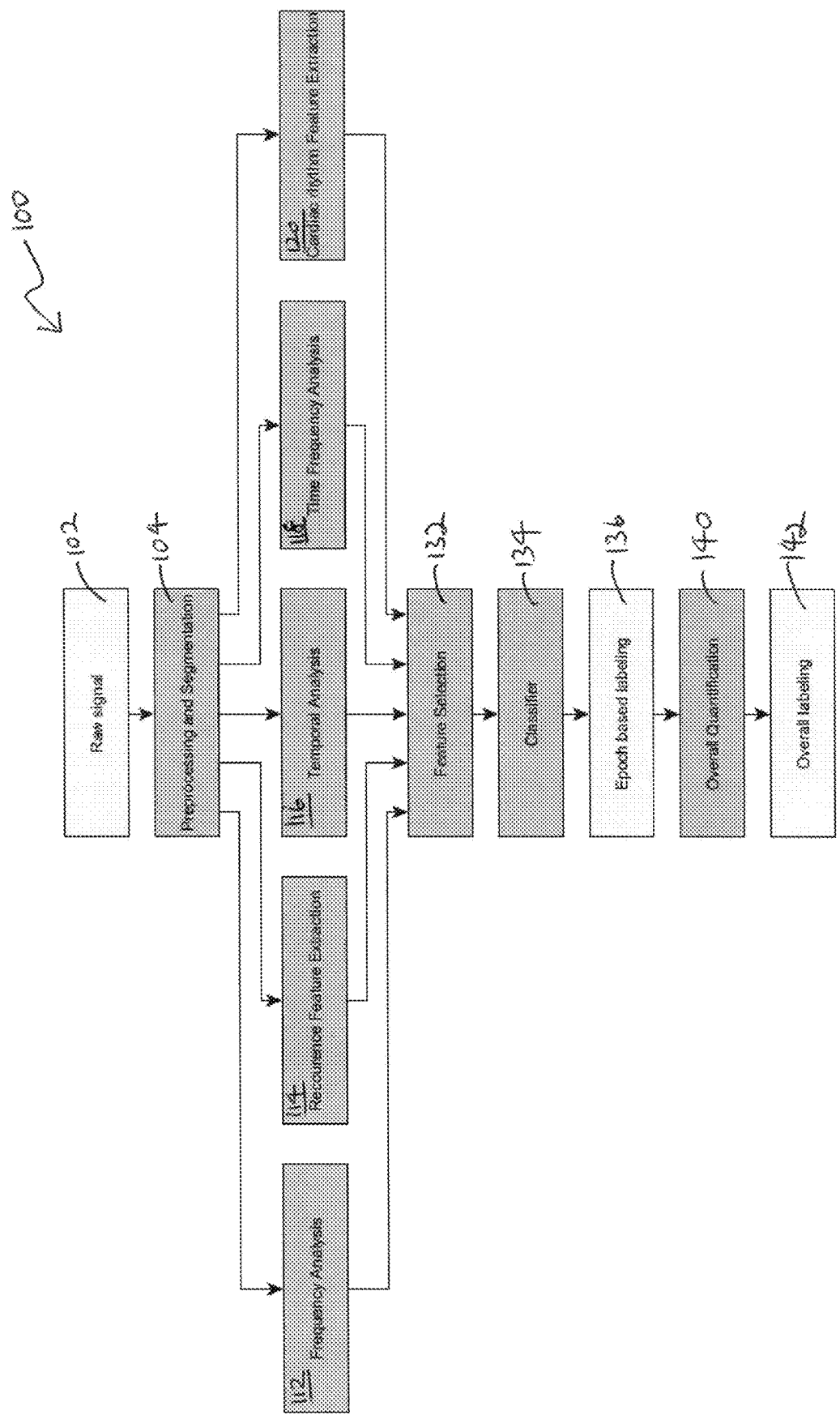
FIG. 1 depicts a flowchart of a feature selection method in accordance with an embodiment of the inventive concept.

FIG. 1 depicts a flowchart of a feature selection method 100 in accordance with an embodiment of the inventive concept. As shown, raw signals (raw BCG signals, for example) are collected from a person (102), and the collected raw signals are subjected to preprocessing and segmentation (104) to generate envelope signals. The envelope signals are used for frequency analysis (112), recurrence feature extraction (114), temporal analysis (116), time frequency analysis (118), and cardiac rhythm feature extraction (120). From these five analyses, feature selection is made (132), classified (134), and epoch-based labeling (136) is done to label each epoch, or time-window. Overall quantification (140) is performed to enable overall labeling (142) as Cardiac Arrhythmia or normal.

Preprocessing

Pre-processing is done on raw data to obtain energy entropy or "envelope signal." Raw data recordings of physiological signals (e.g., taken from a monitoring device such as ECG, BCG, or PPG) is preprocessed. Preprocessing is done for the purpose of noise reduction and extraction of periodicity information. For example, PPG signals may be filtered to 0.5 Hz-4 Hz, and BCG signals may be filtered to 4 Hz-12 Hz. During preprocessing, features such as beat locations and signal transform may be calculated.

Figure 4:
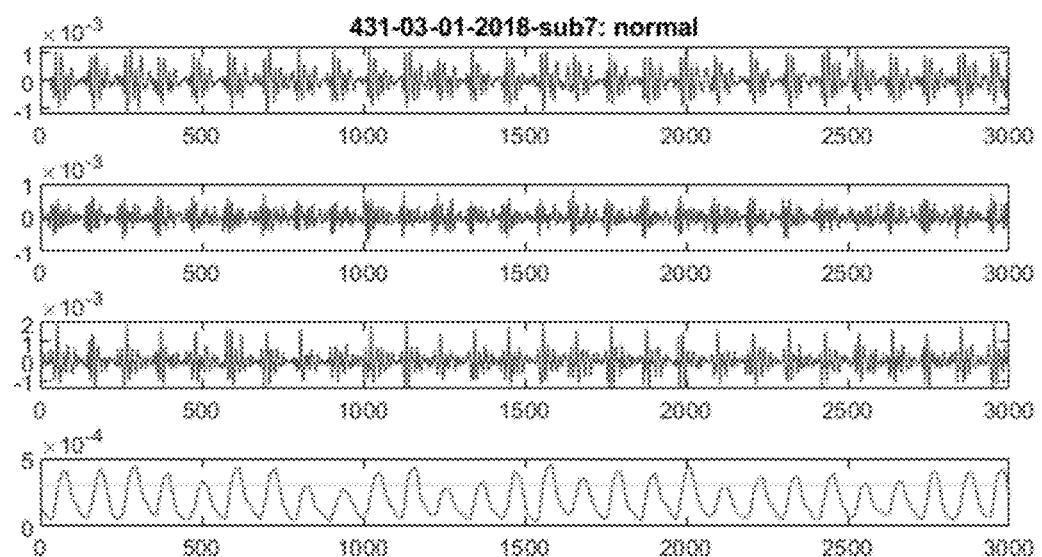
FIG. 4 depicts raw BCG signals and an envelope signal in "normal" state.

Examples of raw BCG signals are shown in the top three plots of FIG. 4, for example. BCG measures body acceleration caused by cardiac output as well as respiration movements. Typically, BCG signals correspond to movements coaxial with the human body. BCG signals may be collected from various body locations of a person. The three raw signals shown in and FIG. 4 may be from three channels, either from multiple sensors detecting motion in X, Y, and Z directions or a single sensor with multiple channels. This is, however, not a limitation of the inventive concept and there may be more or fewer channels for raw signals.

As can be seen, the raw BCG signals are complex because they contain multiple peak events during one heartbeat. The peaks may be categorized into three major groups: pre-systolic, systolic, and diastolic. Due to the complexity of the BCG signal and the harmonic pattern of the BCG signal, it may be challenging to determine a heartrate and a respiration rate directly from a raw BCG signal. Accordingly, the BCG signal is processed to determine the heart rate and respiration rate.

As part of processing, pre-processing may be performed using the method disclosed in U.S. Patent Application Publication No. 2017/0273635, for example. In that method, an ideal BCG signal is modeled as:

$$BCG(t) = A \cdot \sin\left(\frac{2\pi f_{HR} t}{k}\right) \cdot \sin(2\pi f_{HR} t) \cdot (B \cdot \sin(2\pi f_{RR} t + \varphi)) + \delta$$

where A refers to a weight of cardiac-related components, B refers to a weight of respiratory components, $f_{HR}$ refers to a heartbeat frequency, $f_{RR}$ refers to a respiration frequency, k refers to a harmonic factor of heartbeat, φ refers to a respiratory phase shift, and δ refers to noise and artifacts.

Figure 2:
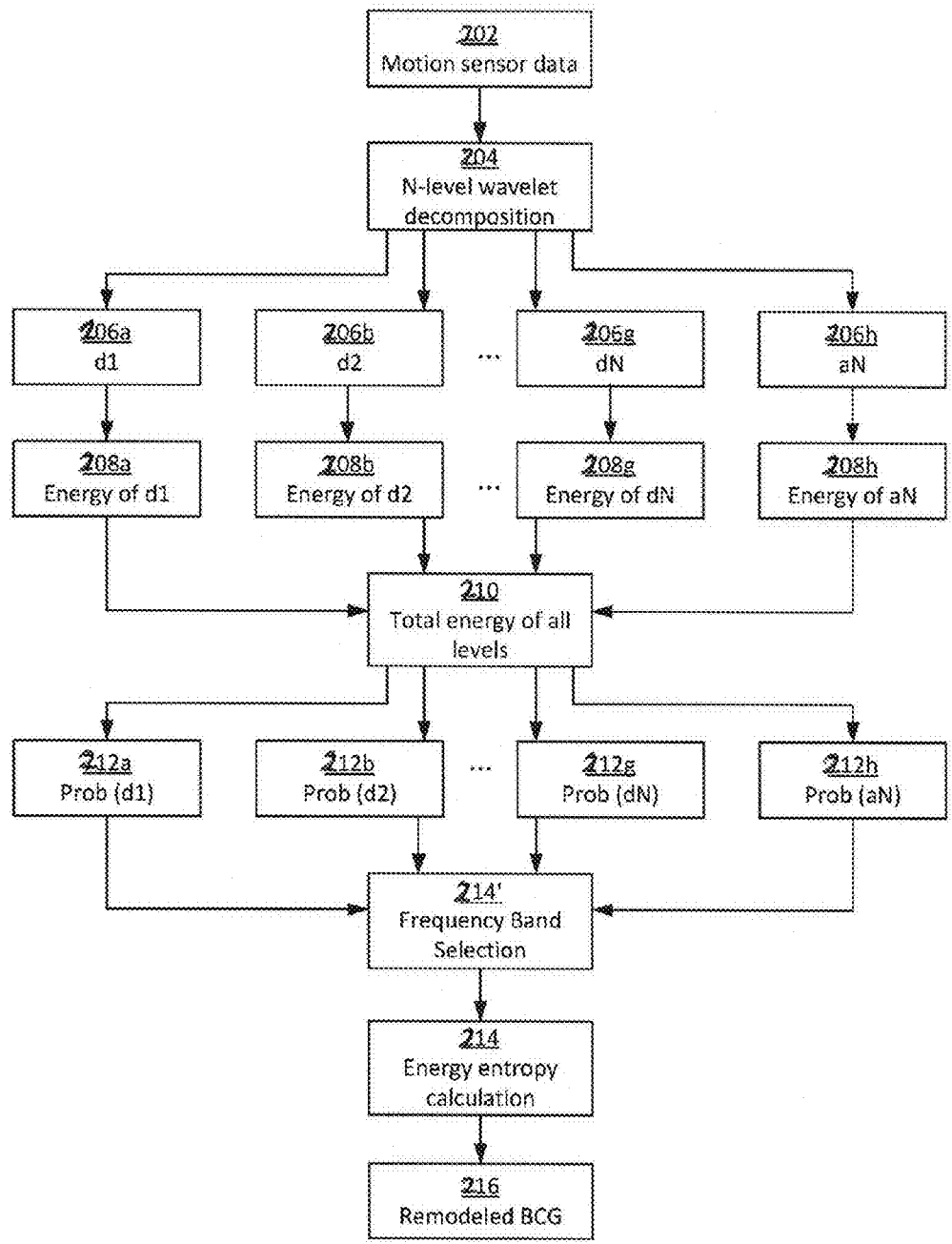
FIG. 2 depicts a flowchart for an example method of preprocessing.

FIG. 2 depicts a flowchart for preprocessing by reconstructing decomposed BCG signals according to a method that is disclosed in U.S. Patent Application Publication No. 2017/0273635, as a way of example. Referring to FIG. 2, various sensors detect motion (including acceleration) in different directions (202). The raw motion data may be decomposed using N-level wavelet decomposition. The decomposition may be performed (204), for example, by a decomposition module (shown in FIG. 20). This may result in the decomposed signals at 206a to 206h.

In some cases, a moving average energy entropy may be used for the reconstruction process. A sliding window may be used to calculate moving average energy. In each window instance, energy-entropy is described in Equations 1-3 below. A sliding window with a desired window size based on specific use may be used. Additionally, multi-window based reconstruction may be applied in some cases.

At 208a to 208h, an energy calculation may be made for reach of the decomposed signals. Depending on the architecture, the calculations may be made by a decomposition module 250, a reconstruction module 260, a processor 112, and/or a CPU 200 described in reference to FIG. 20. The energy calculation may use Equation (1):

$$\text{Energy}_i = \Sigma(i\text{th decomposed signal})^2 \quad (1)$$

At 210, the individual energy levels may be collected to calculate the probability distribution of the decomposed signals 206a-206h. The individual probability may be calculated using Equation (2):

$$Prob_i = \frac{Energy_i}{\sum_{k=1}^{N} Energy_k} \quad (2)$$

The individual probabilities at 212a to 212h may be used to calculate the entropy S of the signals, as shown in Equation (3):

$$S = \Sigma_{i=1}^{N} Prob_i \cdot \ln(Prob_i) \quad (3)$$

Various embodiments may use the entropy S to calculate the Boltzmann entropy $S_B$ to reconstruct a reconstructed signal from the decomposed signals 206a-206h:

$$S_B = Nk_B \Sigma_{i=1}^{N} Prob_i \cdot \ln(Prob_i) \quad (4)$$

By adjusting the Boltzmann constant $k_B$, various embodiments of the present disclosure may develop an adaptive weight for each sliding window. Accordingly, the various embodiments may further provide time domain smoothing techniques including, but not limited to, moving average and maximum modulus principle based on specific use cases.

At 214, one or more frequency bands corresponding to, for example, 206a to 206h may be selected. Equations 3 and 4 may be used to make energy entropy calculations of the selected frequency bands. FIG. 3A shows an example energy entropy plot. The energy entropy calculations may then be used at 216 to reconstruct the BCG signal from the decomposed BCG signal in order to generate an envelope signal. Various embodiments may use lower frequency bands, such as the VLF bands for determining respiration rates and/or phases of respiration.

The method of FIG. 2 is an example, and not the only method for reconstructing decomposed BCG signals.

FIG. 4 shows three raw signals and a preprocessed, reconstructed BCG signal that is herein referred to as envelope signal. Information from the envelope signal may be further extracted for downstream methods to determine heart rate variability (HRV), sleeping quality, and stress.

Feature Extraction

The general concept of feature extraction is known in signal processing. In accordance with the inventive concept, feature extraction is done using the envelope signal, not the raw signals. The features explicitly disclosed in this disclosure include frequency-domain features, recurrence features, time-domain features, time-frequency domain features, and cardiac rhythm features. Each of these extraction processes will be described more in detail below.

FIG. 3A depicts an envelope signal (energy entropy) calculated from a tri-axial signal. Where BCG data is used as raw signal (FIG. 1A), w denotes the total entropy. For each epoch or time-window, the mean entropy $\overline{w}$ is calculated. The epoch with mean entropy $\overline{w}$ more than three scaled median absolute deviations (cMAD) away from the median is annotated as "motion." For one patient recording made up of N epochs, the scaled median absolute deviation (cMAD) is defined as $$cMAD = cmed(|\overline{w} - med(\overline{w})|)$$

for i=1, 2, . . . , N, where c=−1/(sqrt(2)*erfcinv(3/2)). The horizontal line in FIG. 3B shows the motion threshold (cMAD away from the median).

In the particular example shown in FIG. 3A, FIG. 3B, and FIG. 3C, recordings from 12 out of 47 patients were grouped into 17476 epochs. FIG. 3B depicts the summed energy entropy of 12 patients using a sliding window. Among them, 7864 epochs were detected as motion artifacts. The number of normal (sinus rhythm), AFib, and noise epochs are 2474, 2537, and 4601, respectively.

Recordings from the remaining 35 subjects were parsed and prepared for further AFib screening test. The motion rejection algorithm was applied on every epoch so that each epoch was annotated as "motion" or not. The plot of FIG. 3C shows motion annotated from the second plot. If, in a given window, cumulated value is above motion threshold, it will be labeled as motion in FIG. 3C.

A set of statistical features are calculated for each epoch, as shown in TABLE 1.

TABLE 1

| | | |
|---|---|---|
| 1 | Shannon entropy of PSD of energy entropy | E[PSD(w)] |
| 2 | Minimum of envelops of x, y, z axis signals | min[Env(x), Env(y), Env(z)] |
| 3 | Minimum Shannon entropy of PSD of x, y, z axis entropies | min[E[PSD($w_x$)], E[PSD($w_y$)], E[PSD($w_z$)]] |
| 4 | Standard deviation of IBIs | min[std($IBI_x$), std($IBI_y$), std($IBI_z$)] |

TABLE 1-continued

| | | |
|---|---|---|
| 5 | Differences of median filtered IBIs | $\min_i [\|\mathrm{median}(IBI_i, W) - \mathrm{median}(IBI_i, W+1)\|_2]$ |
| 6 | Determinism of recurrence plot (the percentage of recurrence points forming diagonal lines) of energy entropy | $\mathrm{Det}[P_d(w)]$ |
| 7 | Kurtosis (skewness) of energy entropy | $\mathrm{kurtosis}(w)$ |
| 8 | Minimum peak-to-peak amplitude of x, y, z axis signals | $\min[\max(x) - \min(x), \max(y) - \min(y), \max(z) - \min(z),]$ |
| 9 | peak-to-peak amplitude of energy entropy | $\max(w) - \min(w)$ |
| 10 | Laminarity of recurrence plot (the percentage of recurrence points forming large horizontal lines) of energy entropy | $\mathrm{Lam}[P_h(w)]$ |
| 11 | Shannon entropy of horizontal structures in recurrence plot of energy entropy | $E[P_h(w)]$ |
| 12 | Standard deviation of time-averaged spectrogram | $\min_i [std(\overline{S_{wi}}(f))]$ |
| 13 | Minimum standard deviation of peak positions in spectrogram | $\min_i [std(\mathrm{Peak}_{wi}(f))]$ |
| 14 | Minimum standard deviation of peak widths in spectrogram | $\min_i [std(\mathrm{Width}_{wi}(f))]$ |
| 15 | Shannon entropy of PSD of energy entropy | $E[PSD(w)]$ |
| 16 | Minimum Shannon entropy of PSD of x, y, z axis entropies | $\min[E[PSD(w_x)], E[PSD(w_y)], E(PSD(w_z))]]$ |

In Table 1, the probabilities used in Shannon entropy in Feature 1, 3 and 15, 16 are different. Shannon entropy is given by $$E = -\Sigma p \ln p,$$

where in Feature 1 and 3, for every frequency between $f_{min}$ and $f_{max}$, the following boundaries are used:

$$p = PSD(w)/\Sigma_{f_{min}}^{f_{max}} PSD(w).$$

In contrast, in Feature 15 and 16, the following equation is used:

$$p = PSD(w)/\Sigma_0^{f_s} PSD(w).$$

Five example features will now be described in detail.

Figure 5:
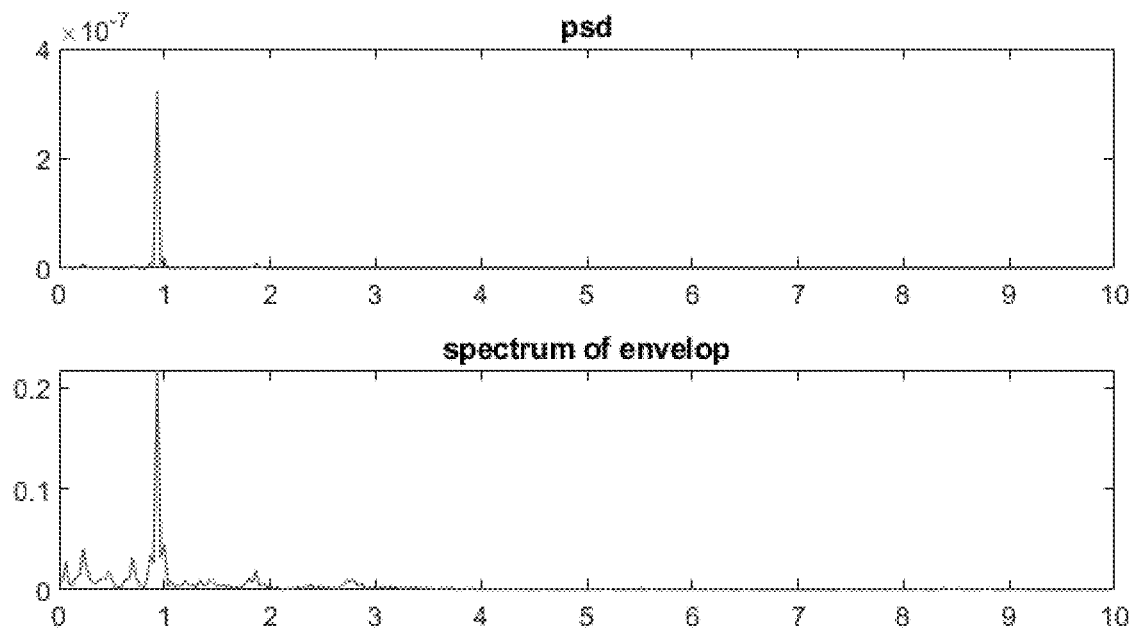
FIG. 5 depicts the power spectral density feature of the energy entropy and the entropy of spectrum feature of envelope signal in "normal" state.
Figure 6:
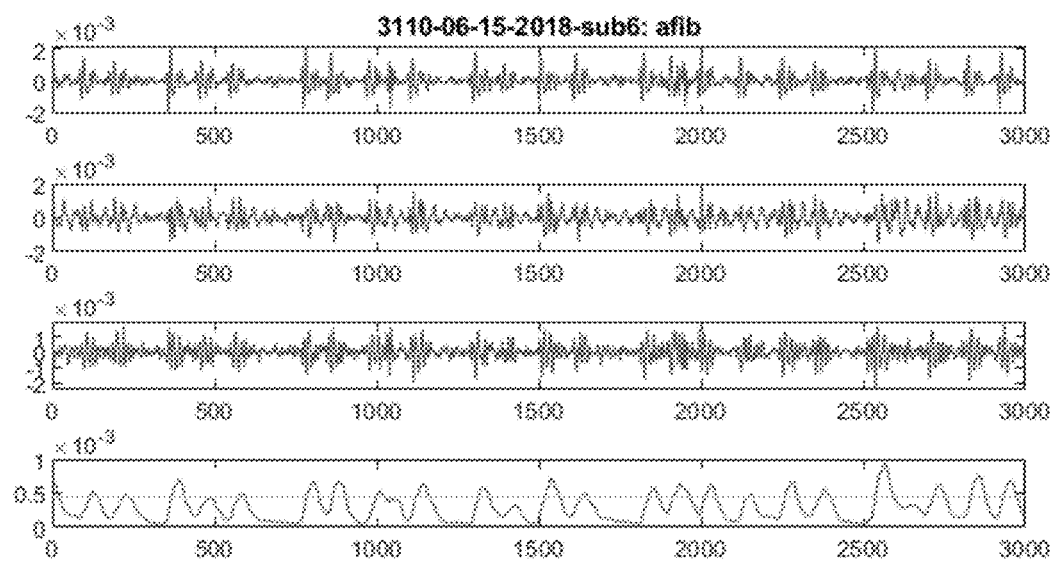
FIG. 6 depicts raw BCG signals and an envelope signal in "afib" state.
Figure 7:
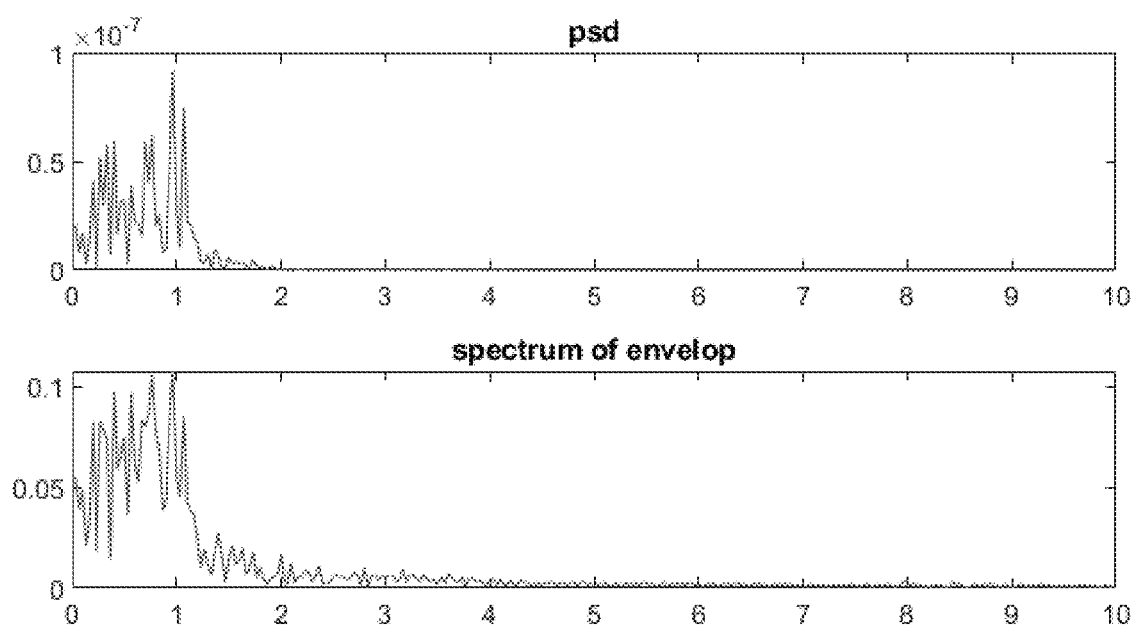
FIG. 7 depicts the power spectral density feature of the energy entropy and the entropy of spectrum feature of envelope signal in "afib" state.
Figure 8:
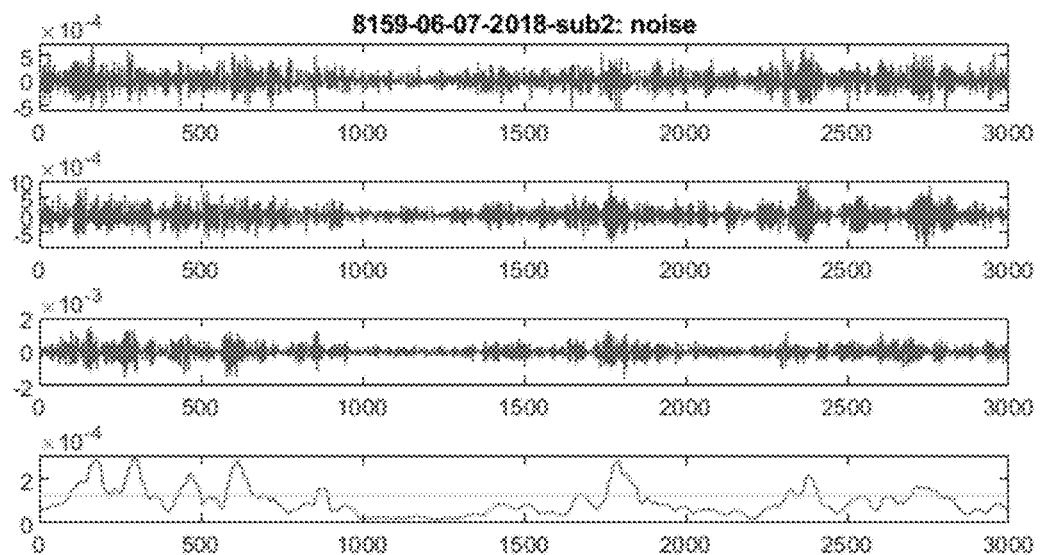
FIG. 8 depicts raw BCG signals and an envelope signal of "noise" state.
Figure 9:
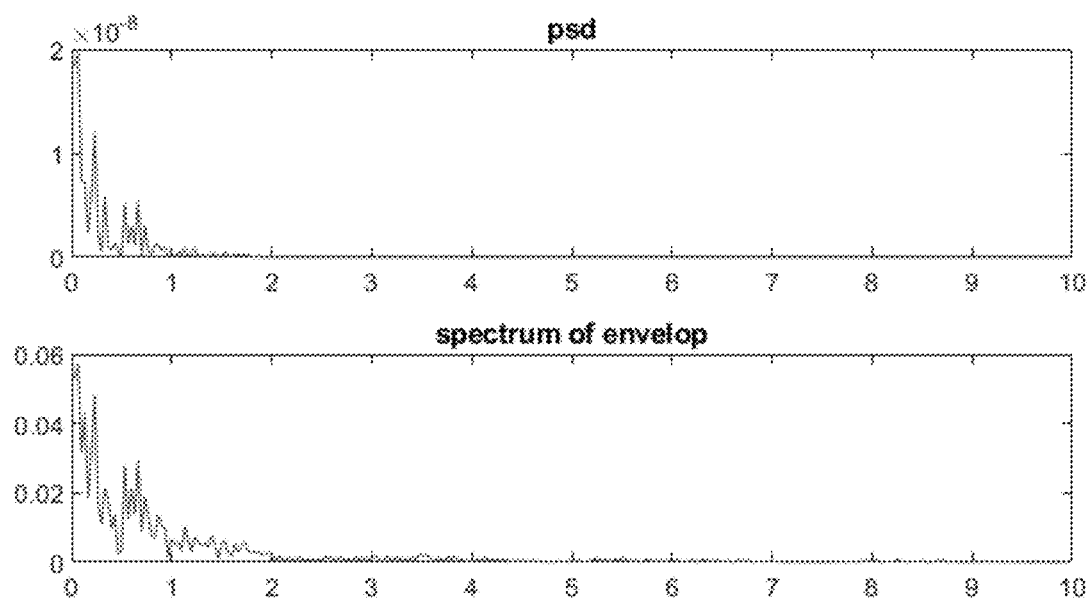
FIG. 9 depicts the power spectral density feature of the energy entropy and the entropy of spectrum feature of envelope signal of "noise"

Frequency-Domain Features are Features 1 and 15 in Table 1. The variables $x_i$, $x_{fi}$, $w_i$ (i=1,2,3) denote the tri-axial raw BCG signals, the filtered signals, and entropy signals, respectively. Energy entropy w is calculated using the filtered signals. The power spectral density (PSD) of energy entropy is denoted as $P_w(f)$ where f is the frequency in Hz. In FIG. 4, which shows three raw BCG signals in "normal" state, also shows the envelope signal (energy entropy) as the fourth plot. FIG. 5 shows the power spectral density (PSD) of the energy entropy (feature 1 in Table 1), and the entropy of spectrum of envelope (feature 2 in Table 1). FIG. 6 shows the three raw BCG signals in "afib" state and a fourth plot showing the envelope signal. FIG. 7 show the PSD and the spectrum of envelope extracted from the envelope signal in FIG. 6. FIG. 8 and FIG. 9 show the same set of plots for "noise."

Referring to FIG. 5, the PSD or spectrum of envelop of normal sinus rhythm shows a significant peak at the frequency of a beating heart (around 1 Hz in this example). FIG. 7 shows that the PSD during Afib shows multiple peaks with larger full width at half maximum (FWHM). The features are computed as the entropy of the PSD. These features may enable distinguishing normal sinus rhythm from the others. There are two different ways to define the probability in an entropy:

$$\mathrm{Prob}_{f,1} = \frac{P_w(f)^2}{\sum_{f=0.5Hz}^{3Hz}(P_w(f))^2} \text{ or}$$

$$\mathrm{Prob}_{f,2} = \frac{P_w(f)^2}{\sum_{f=0}^{f_s/2}(P_w(f))^2},$$

where f is limited in 0.5 Hz≤f≤3 Hz. Then the frequency-domain features are defined using the entropy of $P_w(f)$ with the two definitions of probability, respectively, as $$\mathrm{Entropy}_i = -\sum_f \mathrm{prob}_{f,i} \cdot \log(\mathrm{prob}_{f,i}).$$

Feature 3 is the minimum of entropies of $P_{x_{fi}}(f)$, for i=1, 2, 3.

The envelop of signals may be extracted using the Hilbert transform denoted H(•). In this case, the spectrum of envelope is calculated.

Recurrence Features are Features 6, 10, and 11 in Table 1. Recurrence plot is a powerful tool to visualize the periodic property of a signal. It depicts the collection of pairs of times at which a state of the signal recurs, i.e., the set of (i,j) with s(i)≈s(j). The recurrence plot can be expressed explicitly as $$R(i,j) = \Theta(\epsilon - \|s(i) - s(j)\|), s \in R^M, i,j = 1, \ldots, N,$$

where N is the length of signal, ϵ is a threshold parameter and Θ(•) is the Heaviside function. Feature 6, Feature 10, and Feature 11 are extracted from the recurrence plot of entropy signal w. So the state s of a signal w is given by s(i)=[w(i), w(i+τ), . . . , w(i+(M−1)τ)], where M is the number of neighbors and τ is the delay parameter.

Recurrence plot is useful for distinguishing the epochs with different labels. For instance, if the entropy w is strictly periodic with period T, which only happens in the epoch with normal rhythm, then all such pairs of times (i,j) will be separated by a multiple of T and be visible as diagonal lines in the plot. Three statistical features were selected in order to quantify the texture of recurrence plot. Feature 6 computes the entropy of the histogram distribution of diagonal lines. Feature 10 and Feature 11 quantify the histogram distribution of horizontal lines by calculating its laminarity (percentage of large values) and entropy, respectively.

Figure 10:
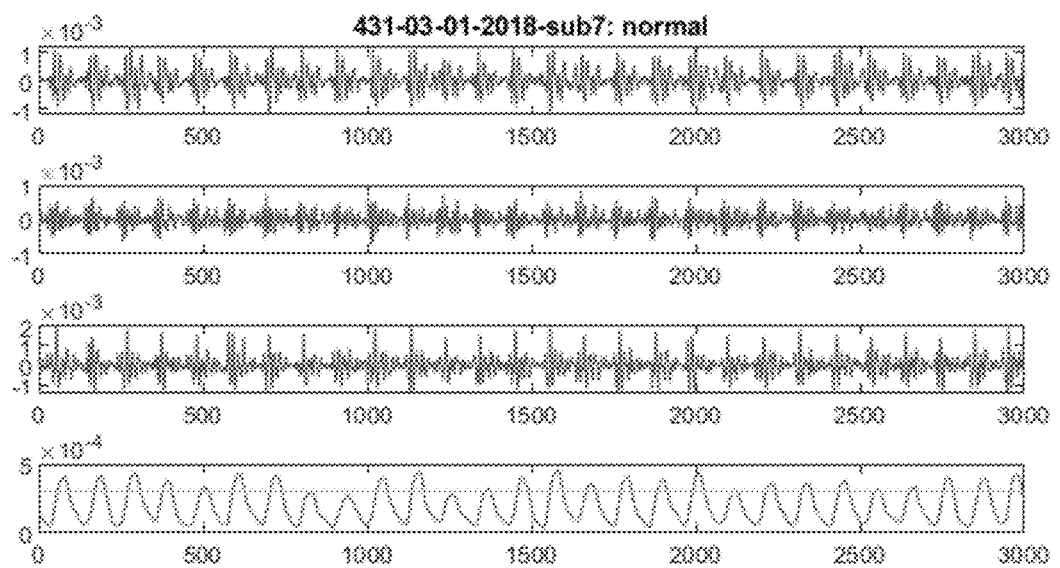
FIG. 10 depicts trial-axial raw signals and the envelope signal of an example "normal" state.
Figure 11:
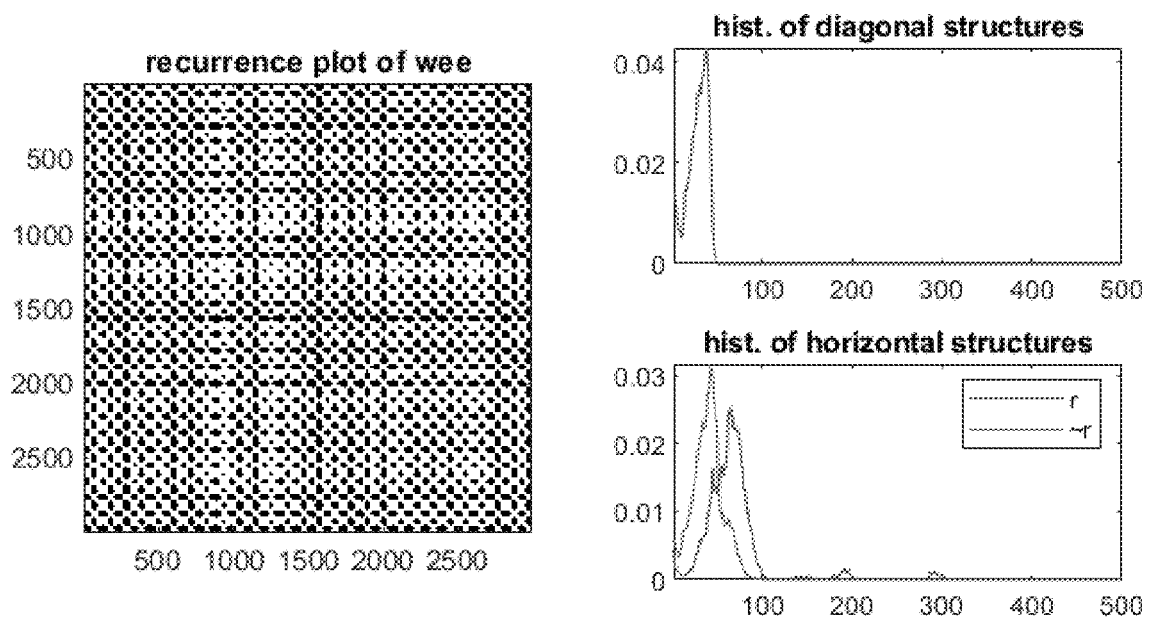
FIG. 11 depicts the recurrence plot, histogram distribution feature of diagonal lines, and the histogram distribution feature of horizontal lines in the "normal" state.

FIG. 10 shows the three raw signals and the envelope signal of an example "normal" sinus rhythm state. The left side of FIG. 11 shows a recurrence plot generated from the fourth plot of FIG. 10. The plot on the upper right side of FIG. 11 depicts the histogram distribution of diagonal lines based on Feature 6. The plot on the lower right side of FIG. 11 depicts the histograms distribution of horizontal lines based on Features 10 and 11.

Figure 12:
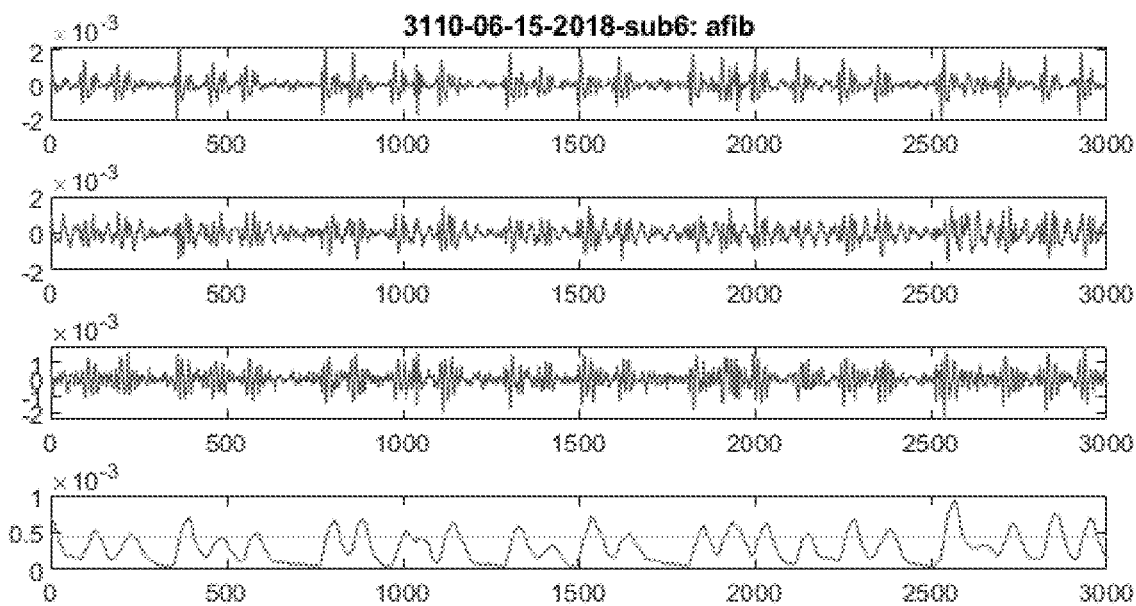
FIG. 12 depicts trial-axial raw signals and the envelope signal of an example "afib" state.
Figure 13:
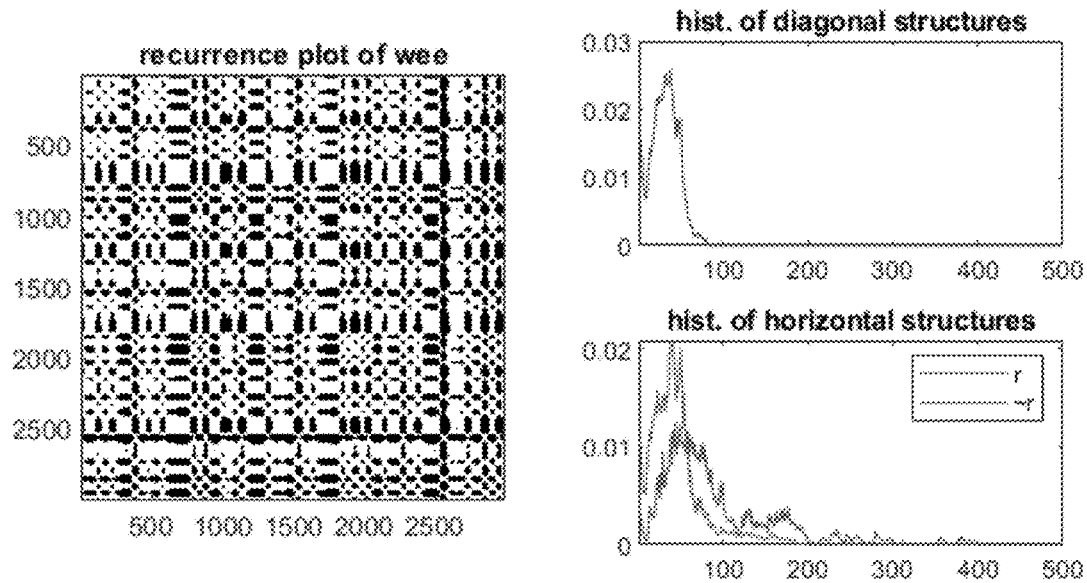
FIG. 13 depicts the recurrence plot, histogram distribution feature of diagonal lines, and the histogram distribution feature of horizontal lines in the "afib" state.
Figure 14:
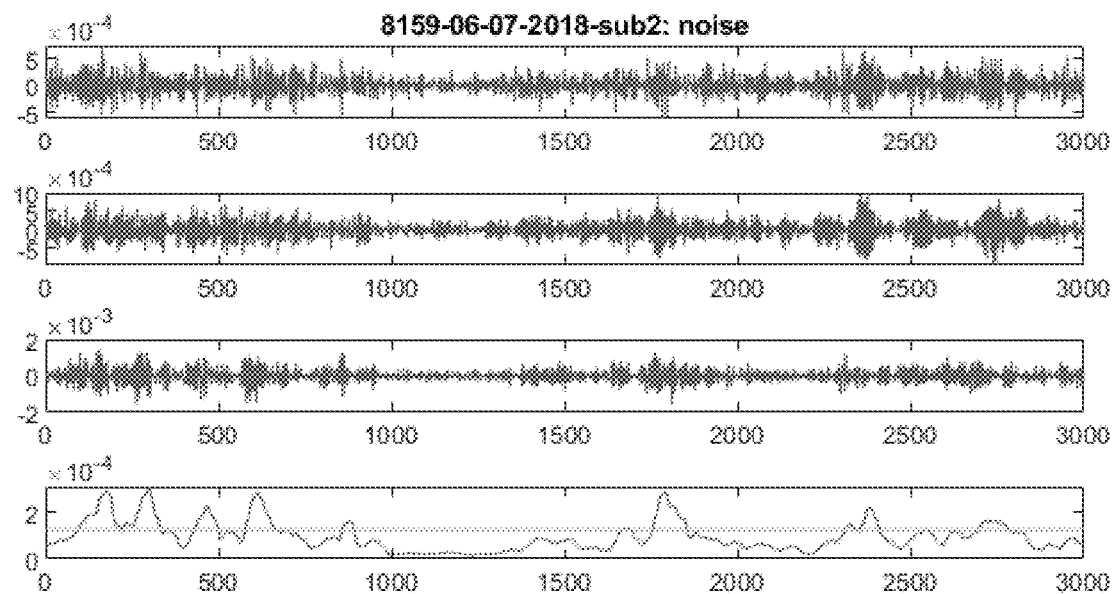
FIG. 14 depicts trial-axial raw signals and the envelope signal of an example "noise"
Figure 15:
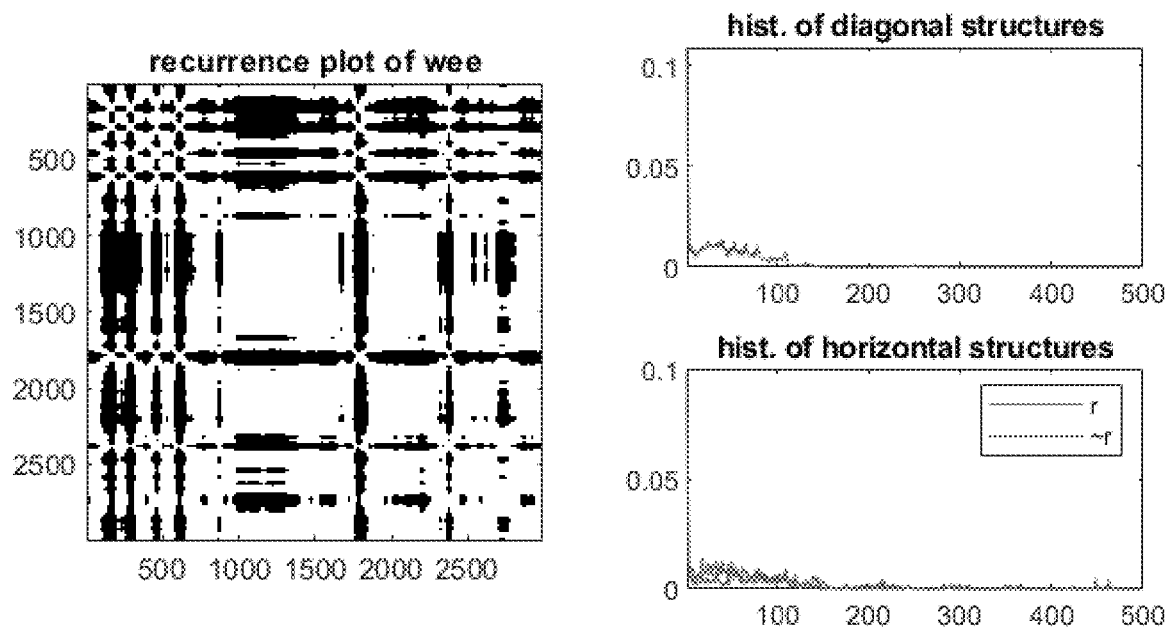
FIG. 15 depicts the recurrence plot, histogram distribution feature of diagonal lines, and the histogram distribution feature of horizontal lines of "noise"

FIG. 12 and FIG. 13 depict the raw signals, the envelope signal, the recurrence plot, the histogram of diagonal structures, and the histogram of horizontal lines for "afib" state. FIG. 14 and FIG. 15 depict the same set of plots for the "noise" channel.

Time-Domain Features are Features 7, 8, and 9 in Table 1. Three time-domain features are included in this example. Feature 7 is the skewness of energy entropy w. Artifacts and other rhythms, such as respiratory artifacts and rhythms, tend to cause amplitude variations and outliers which are reflected in this statistical metric. The same is true for the maximal peak-to-peak amplitude during the epoch. Feature 8 and Feature 9 are the minimal peak-to-peak amplitudes of raw signals $x_i$ and signal entropies $w_i$ in three channels, $$\text{i.e., } \min_{i=1,2,3} [\max(x_i) - \min(x_i)] \text{ and } \min_{i=1,2,3} [\max(w_i) - \min(w_i)],$$

respectively. These two features should increase in comparison to sinus rhythm epochs in the presence of noise.

Time-Frequency Domain Features are Features 12, 13, and 14 in Table 1. To represent the short duration behaviors of the BCG signal, time-frequency distributions are widely used and can offer insights into the properties of signals. A spectrogram, which is a time-varying spectral representation, is obtained by means of the short-time Fourier transform (STFT). To capture the small motion artifacts, 5-second rectangular windows with 4 seconds of overlapping in STFT was used. The spectrogram of a segment of entropy w is denoted as $S_w(t,f)$. $\overline{S_w}(f)$, which is the time-averaged frequency spectrogram, and is generated by the summation of $S_w(t,f)$ along the time axis.

Figure 16:
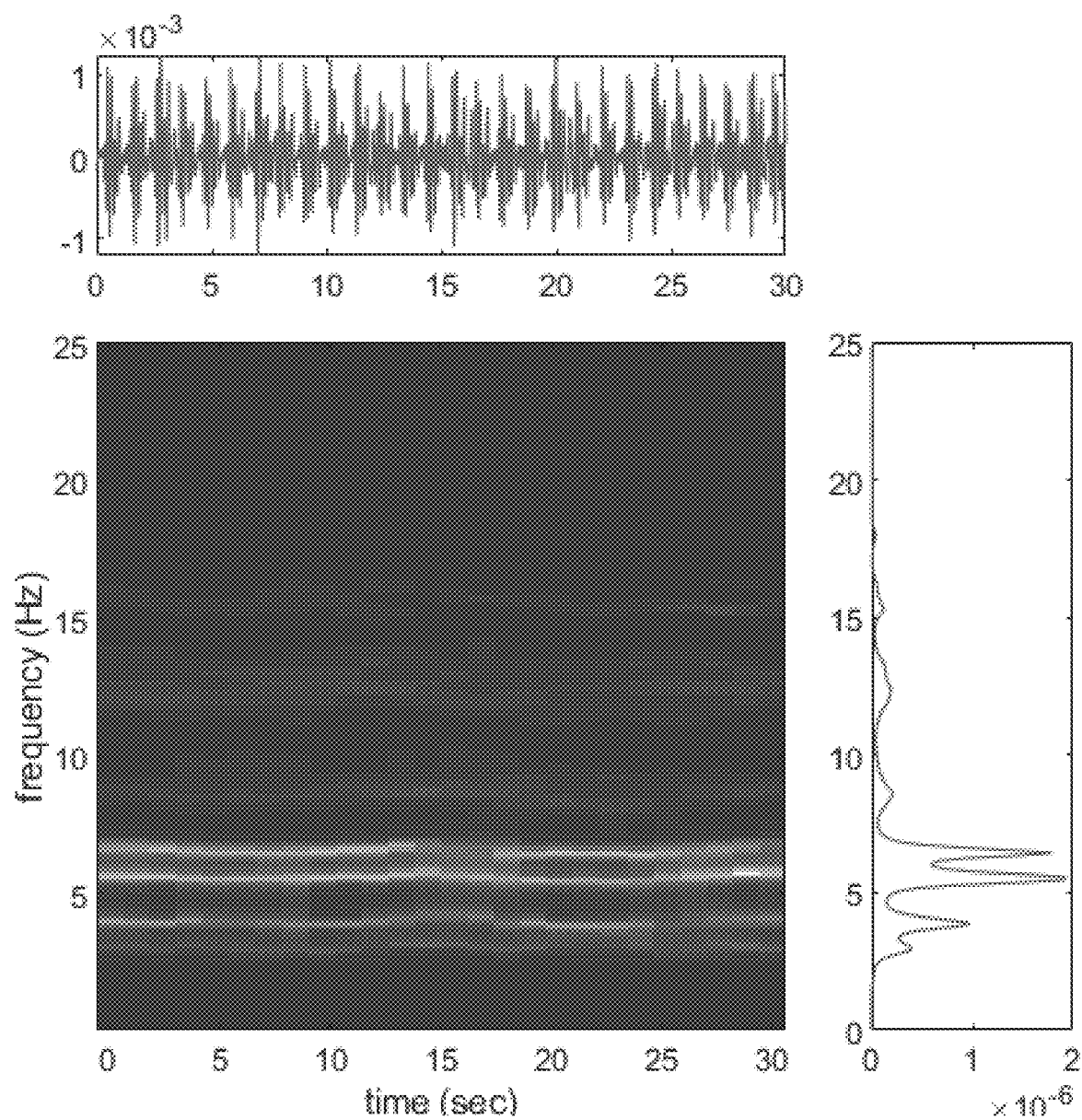
FIG. 16 depicts raw signals, the resulting spectrogram, and a feature plot of a "normal" state.
Figure 17:
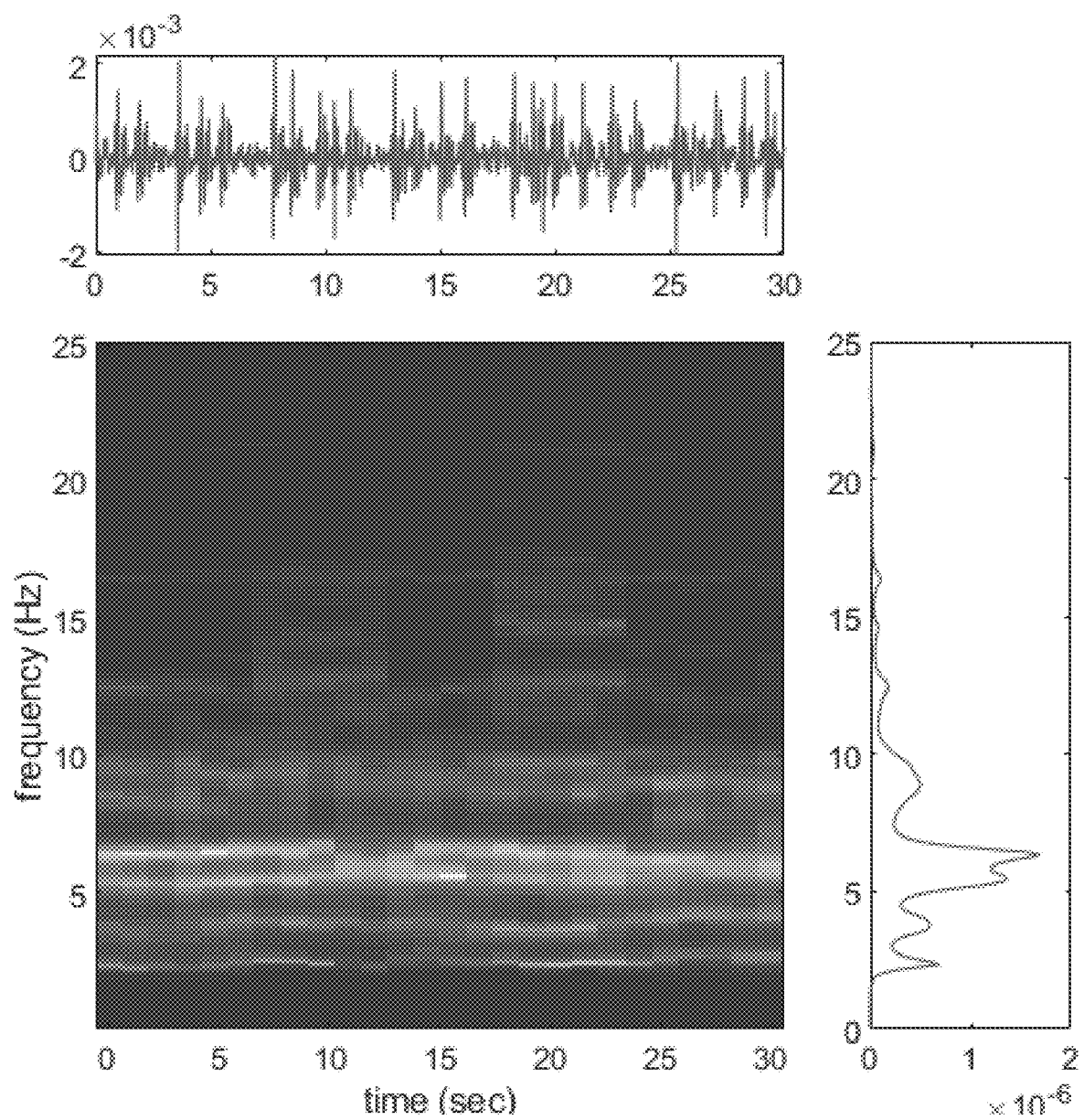
FIG. 17 depicts raw signals, the resulting spectrogram, and a feature plot of an "afib" state.
Figure 18:
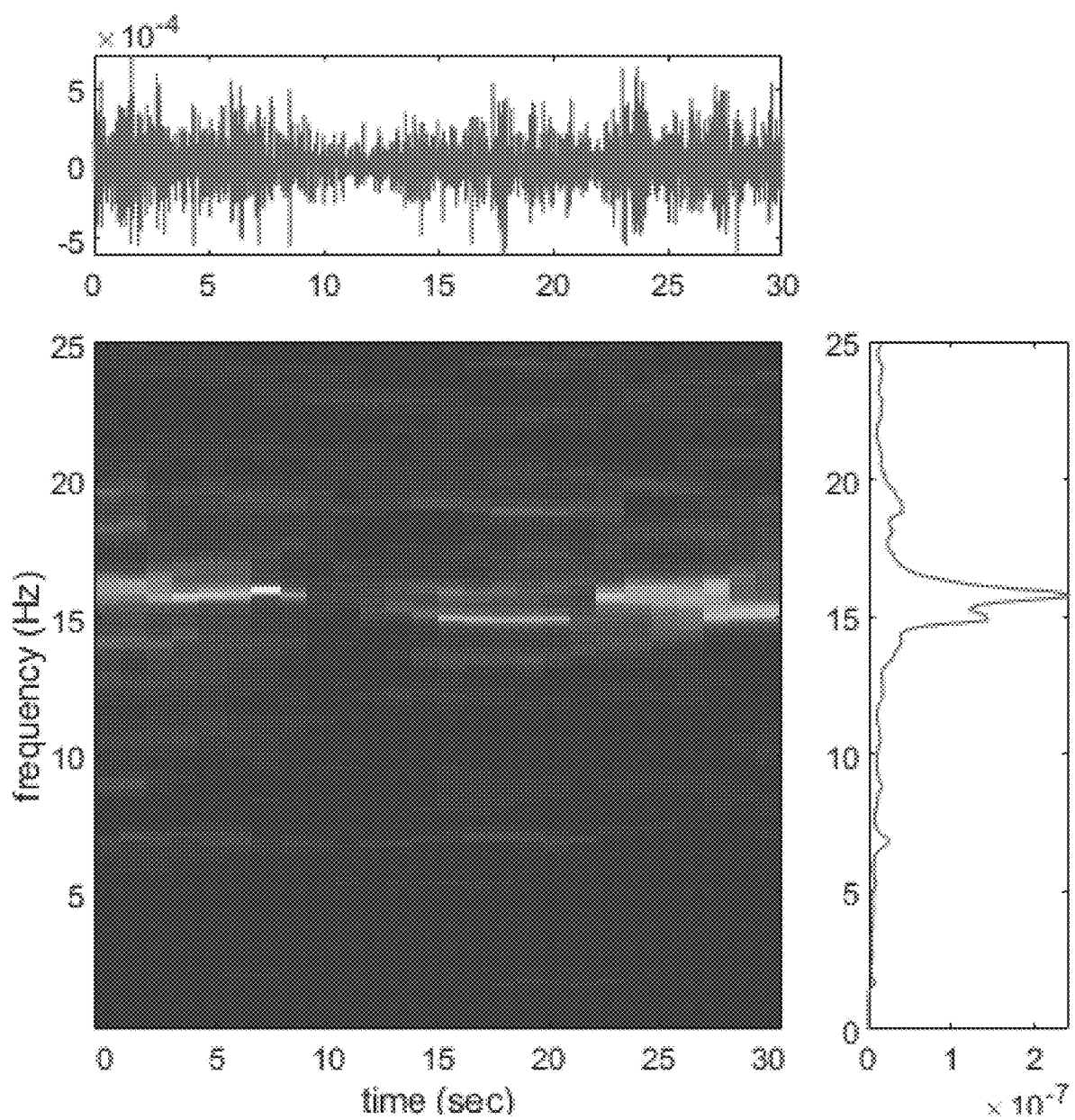
FIG. 18 depicts raw signals, the resulting spectrogram, and a feature plot of for "noise"

The spectrograms of a sinus rhythm epoch, shown in FIG. 16, FIG. 17, and FIG. 18, depict clearly discernible pattern of distinct lines. These lines correspond to the base frequency of the heart rate and its harmonics. FIG. 16 depicts the spectrogram (shown as the square plot) in a "normal" state, FIG. 17 depicts the spectrogram in an Afib state, and FIG. 18 depicts the spectrogram for the "noise." The spectrograms during Afib appear smeared as the lines representing the base frequency varies along time. For each frequency slice of the spectrogram, the largest local maxima (peak) with its height, index, width and prominences is found. Feature 12 is the standard deviation of $\overline{S_w}(f)$. Feature 13 and Feature 14 are standard deviation of the indices and widths of the peaks, respectively. Larger values are expected in Feature 13 and Feature 14 during the epochs with Afib.

In addition to the spectrograms, each of FIG. 16, FIG. 17, and FIG. 18 depicts the raw signal above the spectrogram and the feature plot to the right of the spectrogram. The feature plots of the three states show distinctive patterns. Features 12, 13, and 14 are extracted, or calculated, from these feature plots.

Cardiac Rhythm Features are Features 4 and 5 in Table 1. Interbeat interval (IBI) has received a great deal of attention in diagnosing arrhythmias. Afib may lead to a rapid and irregular heart rate, which means that the IBI varies significantly in Afib epoch compared to epoch with sinus rhythms. During motions, the heart beat extraction may become inaccurate. To evaluate the randomness of IBI changes, Feature 4 and Feature 5 were calculated. Instead of computing statistical measures of raw IBI, the IBI values are filtered by moving median filters with two different window sizes:

$$I_1 = \text{med}(IBI, K), I_2 = \text{med}(IBI, K+1),$$

where K is the window size. Feature 4 is the minimum of standard deviations of $I_1$ and $I_2$. Feature 5 measures the difference between $I_1$ and $I_2$ by finding the L2 norm of $I_1 - I_2$. Feature 4 is expected to be small in normal rhythm epochs and to be large in epochs with AF or noise. Feature 5 quantifies the variation and irregularity of IBI. This number should increase among noise epochs compared to AF epochs.

Feature Selection

Figure 19:
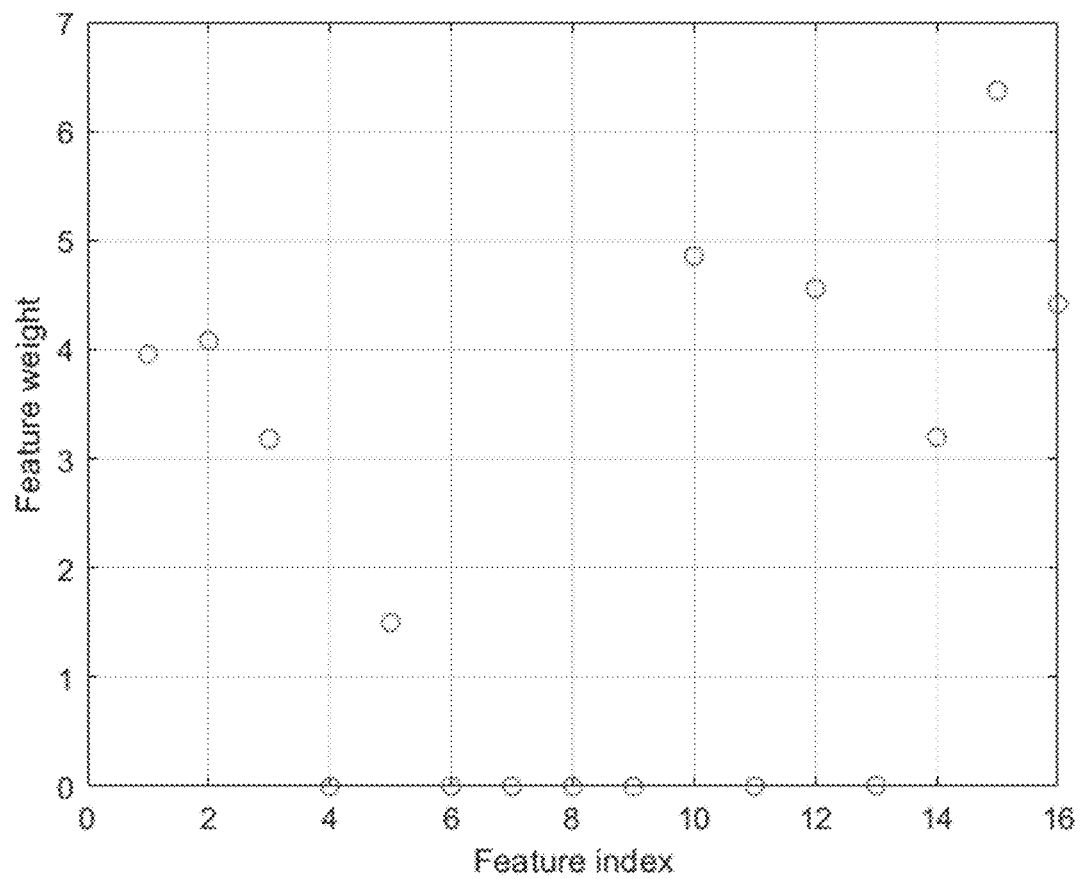
FIG. 19 depicts an example plot of NCA-based feature selection results.

While the features provide valuable information, the information can be made more accurate and clearer by selectively combining features that might provide extra insight into a person's condition. During this selective combination process, some features that are unnecessary or even disadvantageous for the classifier will be filtered out. Different feature selection methods have been proposed to remove the features that are either redundant or irrelevant without losing information. Some example techniques that may be used to achieve this filtering are as follows:

1. Neighborhood Component Analysis (NCA) is a nonparametric and embedded method for selecting features with the goal of maximizing prediction accuracy of regression and classification algorithms. It finds the weights of features the minimize classification error. The graph below, for example, shows the weight that should be attributed to each feature index. FIG. 19 depicts an example plot of NCA-based feature selection results. In this example, there are generally three groups of features: ones to the left side, ones to the right side, and ones with zero feature weight (which may be filtered out).
2. Principle Component Analysis (PCA) explores the embedded features that are linear combinations of input features.

Classifier

Using features that are selected, classifying is done to identify the type of arrhythmia that is present, if any. The classifier may use some or all of the following methods:

1. Bootstrap-aggregated (bagged) decision trees. This bagged decision tree reduces the effects of over-fitting and improves the generalization by combining multiple decision trees. The bagged decision tree grows the decision trees in the ensemble using bootstrap samples of data.
2. Logistic regression. The logistic regression model estimates the parameters of a logistic model, where the log-odds of the probability of an event is a linear combination of independent features.
3. Support vector machine. Support vector machine model is a non-probabilistic binary linear classifier that maps training samples in space into separate categories by finding the maximum margins between groups. In addition, kernel-based support vector machine can efficiently perform as non-linear classifier and map original features into higher-dimensional space.

4. Denoising autoencoder can perform as feature selection layer in a neural network. For example, an autoencoder with 200 inputs as 20 nodes in hidden layers may combine and compress 200 nonlinear input features that are nonlinear into 20 refined features. At the first training stage, autoencoder inputs are raw feature inputs with noise corruption or missing components; the training targets are original features. The noise terms would help the autoencoder to learn inherent feature combination and prevent over-fitting. At the second stage of training, the trained encoder is connected to a supervised classifier (e.g., a fully connected neural network), and the combined network is further trained with labeled data.

5. Recurrent Neural Network (RNN) is a neural network that uses internal state to handle sequence inputs by forming a directed graph along the sequence. Long Short Term Memory (LSTM) units are of an RNN. In one example, an arrhythmia detection framework generates epoch by epoch classification results. Classified labels and corresponding timestamps may be formed as time series data. LSTM can produce overall classification by combining historical labels with current state.

6. Convolutional Neural Network (CNN)+Deep Neural Network. Arrhythmia classification may be converted into image classification task by extending features into two dimensions. For example, recurrent plots may be considered as images and fed into CNN for feature extraction.

The above classifying methods are examples, and other methods may be suitable. In accordance with the inventive concept, a spectrogram is quantified to look for information other than the traditional information. Each feature contains one or more pieces of information well (e.g., periodicity of signal, anomaly events, strong distinction between noise and anomaly, etc.). Since each feature has a strength, combining features selectively can sharpen the information that is being sought or focused on. For example, hypothetically, if Feature 1 is strong at identifying signal vs. noise, and Feature 2 is strong at identifying between a normal signal and an Afib signal, the two outputs can be combined to generate a signal that can distinguish between normal and Afib with high confidence (since noise can be filtered out more accurately). Hence, selectively combining the features helps generate a more accurate prediction.

Figure 20:
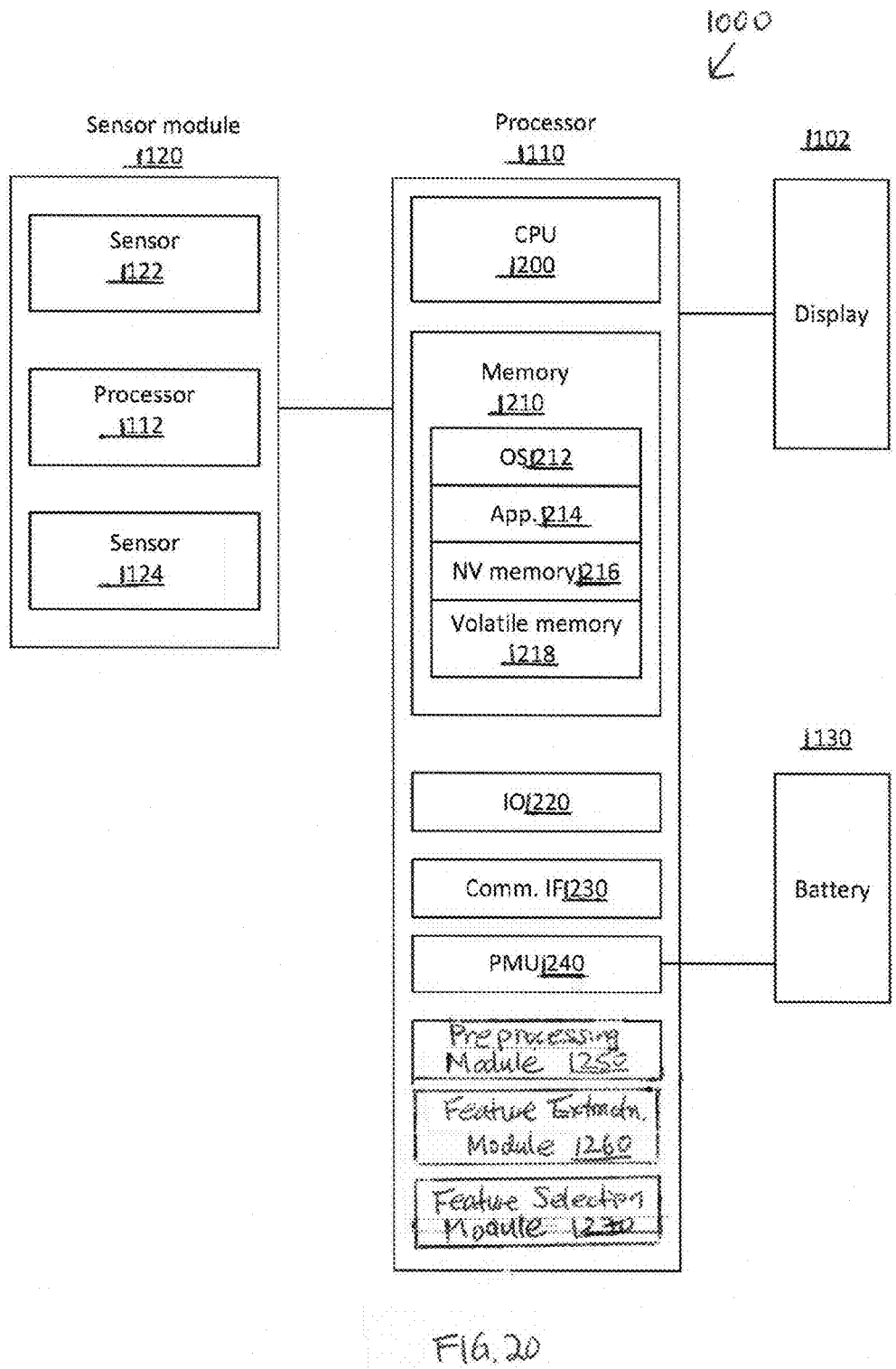
FIG. 20 is a high-level block diagram of an electronic device that may be used to implement an embodiment of the inventive concept.

FIG. 20 is a high-level block diagram of an electronic device that may be used to implement an embodiment of the present disclosure. Referring to FIG. 20, there is a display 1102, a processor 1110, a sensor module 1120, and a battery 1130. Output to the display 1102 may be controlled by the processor 1110. The display 1102 may also include input devices (not shown) such as buttons, dials, keys, touch sensitive screen, and microphone.

The processor 1110 may include a CPU 1200, memory 1210, an input/output (I/O) interface 1220, a communication interface 1230, a power management unit (PMU) 1240, a preprocessing module 1250 that handles signal decomposition and reconstruction, feature extraction module 1260, and feature selection module 1270. While the processor 1110 is described as comprising these various devices, other embodiments may use other architectures where the different functionalities are grouped differently. For example, the grouping may be in different integrated circuit chips. Or the grouping may be combining different devices such as the I/O interface 1220 and the communication interface 1230 together.

The CPU 1200 may control operation of the sensor module 1120 as well as receive monitored signals from the sensor module 1120. The CPU 1200 may control the user-wearable device 1100, including processing the monitored signals from the sensor module 1120, displaying the processed signals on the display 102, receiving input from the display 102, interfacing with various devices via the I/O interface 1220 or the communication interface 1230 by executing instructions in the memory 1210. The I/O interface 1220 may be used by the CPU 1200 to interface with the display 1102.

The processor 1112 may operate using different architectures in different embodiments. For example, the processor 1112 may use the memory 1210 to store instructions to execute, or the processor 1112 may have its own memory (not shown) for its instructions. Although some embodiments have separate processors 1110 and 1112, the various embodiments need not be limited so. There may be one processor 1110 that controls the functionality of the electronic device, or there may be multiple processors for the device.

The memory 1210 may include non-volatile memory 1216 and volatile memory 1218. The operating system and applications may be stored in the non-volatile memory 1216. Various embodiments of the disclosure may use different memory architectures that are design and/or implementation dependent.

The communication interface 1230 may allow the device to communicate with other devices via, for example, a wired or wireless protocol such as USB, Bluetooth, Near Field Communication (NFC), and WiFi. The PMU 1240 may control receiving power from an outside source, charging the battery 1130, as well as allocation of power to the different parts of the electronic device.

The preprocessing module 1250 may function to decompose, for example, an input signal such as a BCG signal to multiple frequency bands using time-frequency transforms, and reconstruct, for example, the decomposed signals to generate the envelope signal. The feature extraction module 1260 extracts one or more of the statistical features shown in Table 1 from the envelope signal. The feature selection module 1270 applies NCA or PCA to achieve the desired filtering.

Figure 21:
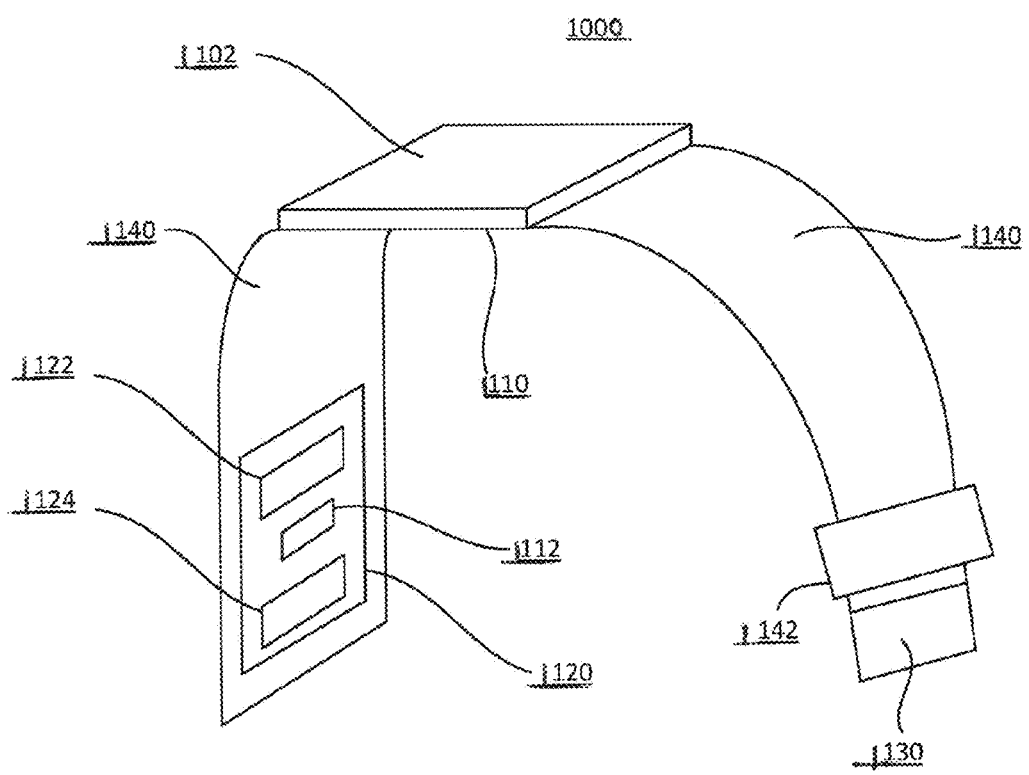
FIG. 21 is a diagram illustrating an electronic device that may be used to implement an embodiment of the inventive concept.

FIG. 21 is a diagram illustrating an electronic device 1000 that may be used to implement an embodiment of the present disclosure. Referring to FIG. 21, the electronic device 1000 may be a user-wearable device that has the display 1102, processors 1110 and 1112, the sensor module 1120, the battery 1130, a band 1140, and a clasp 1142. The sensor module 1120 may include sensors 1122 and 1124 on the side of the strap that contacts the user. Although the particular embodiment of the electronic device 1000 shown in FIG. 21 is designed to be worn around a wrist, this is not a limitation of the inventive concept and the electronic device 1000 may be implemented in various other ways.

The display 1102 may output monitored physiological signals from the user's body for viewing by the user. The signals being monitored may be, for example, heart rate/pulse, pulse morphology, pulse spacing (IBIs), respiration rate, and blood pressure. The display 1102 may also output instructions to the user.

The processor 1110 may receive the monitored signals via a low-powered sensor in the sensor module 1120. The sensor module 1120 may include, for example, the sensors 1122 and 1124 that acquire signals from the user's wrist when the electronic device 1000 is worn by the user. The sensors 1122 and 1124 may be, for example, an accelerometer or motion sensor used to continuously or periodically monitor pulse related information as well as temperature. The processor 1112 may control the sensors 1122 and 1124, and may also process the signals monitored by the sensors 1122 and 1124. For example, the processor 1112 may preprocess the signals monitored by the sensors 1122 and/or 1124, and extract and select features from the preprocessed signals.

The battery 1130 may be configured to provide power for the electronic device 1000. The battery 1130 may be charged using a wired or wireless charging system. The band 1140 may be wrapped around a wrist and held by the clasp 142.

The arrhythmia detection method described above is more robust and accurate compared to existing methods.

While the embodiments are described in terms of a method or technique, it should be understood that the disclosure may also cover an article of manufacture that includes a non-transitory computer readable medium on which computer-readable instructions for carrying out embodiments of the method are stored. The article/apparatus made may include circuits, dedicated and/or programmable, to carry out operations pertaining to embodiments.

It should be understood that the inventive concept can be practiced with modification and alteration within the spirit and scope of the disclosure. The description is not intended to be exhaustive or to limit the inventive concept to the precise form disclosed.

What is claimed is:

1. A method of measuring biological signals of a person, comprising:
    obtaining, via one or more sensors, physiological signals of the person;
    via a processor, converting the physiological signals to an energy entropy signal, determining a plurality of statistical features based on the energy entropy signal, and selecting and combining two or more of the plurality of statistical features;
    wherein the statistical features include two or more of the following:
        Shannon entropy of power spectral density (PSD) of energy entropy;
        minimum envelopes of x-, y-, and z-axis signals;
        minimum Shannon entropy of PSD of x-, y-, and z-axis entropies;
        standard deviation of interbeat intervals (IBIs);
        differences of median filtered IBIs;
        determinism of recurrence plot of energy entropy;
        Kurtosis of energy entropy;
        minimum peak-to-peak amplitude of x-, y-, and z-axis signals;
        peak-to-peak amplitude of energy entropy;
        laminarity of recurrence plot of energy entropy;
        Shannon entropy of horizontal structures in recurrence plot of energy entropy;
        standard deviation of time-averaged spectrogram;
        minimum standard deviation of peak positions in spectrogram; and
        minimum standard deviation of peak widths in spectrogram.

2. The method of claim 1, wherein the physiological signals are ballistocardiogram (BCG) signals.

3. The method of claim 1, wherein the physiological signals are divided into a plurality of epochs, and the statistical features are calculated for each of the epochs, further comprising filtering out signals due to motion, wherein an epoch is classified as motion if a mean entropy $\bar{w}$ of an epoch is more than three scaled-median above deviations (cMAD) away from the median.

4. The method of claim 1, wherein the physiological signals include a first set of signals at "normal" sinus rhythm, a second set of signals under "atrial fibrillation" (afib) conditions, and a third set of signals that represent "noise."

5. The method of claim 1, wherein the Shannon entropy of PSD of energy entropy is $$Entropy_i = -\sum_f prob_{f,i} \cdot \log(prob_{f,i})$$

wherein $prob_{f,i}$ is defined as one of the two following:

$$Prob_{f,1} = \frac{P_w(f)^2}{\sum_{f=0.5Hz}^{3Hz}(P_w(f))^2} \text{ and}$$

$$Prob_{f,2} = \frac{P_w(f)^2}{\sum_{f=0}^{f_s/2}(P_w(f))^2},$$

wherein f is limited to 0.5 Hz≤f≤3 Hz.

6. The method of claim 1, wherein the recurrence plot is expressed as:

$$R(i,j)=\Theta(\epsilon-\|s(i)-s(j)\|), s \in R^M, i,j=1, \ldots, N,$$

wherein N is the length of signal, $\epsilon$ is a threshold parameter and $\Theta(\cdot)$ is the Heaviside function.

7. The method of claim 6, wherein the recurrence plot is a recurrence plot of entropy signal w and the state s of a signal w is given by
    $s(i)=[w(i), w(i+\tau), \ldots, w(i+(M-1)\tau)]$, where M is the number of neighbors and $\tau$ is the delay parameter.

8. The method of claim 1 wherein the spectrogram is generated by applying Short-Time Fourier Transform to the energy entropy signal.

9. The method of claim 1, wherein the standard deviation of IBIs and differences of median filtered IBIs are calculated by filtering IBI values with moving median filters with two different window sizes, such that IBIs are $I_1$ and $I_2$ as defined below:
    $I_1=med(IBI,K), I_2=med(IBI,K+1),$
wherein K is the window size.

10. The method of claim 1, wherein the selecting of two or more statistical features comprises at least one of neighborhood component analysis (NCA) and principle component analysis (PCA).

11. The method of claim 1, wherein the selecting of two or more statistical features comprises using at least one of the following types of neural network:
    a categorical classification neural network;
    denoising autoencoder in a neural network using raw feature inputs with noise corruption or missing components as autoencoder inputs;
    a recurrent neural network; and
    a convolutional neural network with deep neural network.

12. The method of claim 1, wherein the selecting of two or more statistical features comprises using at least one of the following classifiers:

bootstrap-aggregated decision tress;
logistic regression; and
support vector machine.

13. A system for measuring biological signals of a person, comprising:
a sensor module that acquires physiological signals of the person;
a pre-processing module that converts the physiological signals to an energy entropy signal;
a feature extraction module that determines a plurality of features based on the energy entropy signal; and
a feature selection module that selects and combines two or more of the plurality of features.

14. A transitory computer-readable storage medium storing instructions for measuring biological signals of a person, the instructions comprising:
instructions for obtaining, via one or more sensors, physiological signals of the person;
instructions for converting, via a processor, the physiological signals to an energy entropy signal, determining a plurality of statistical features based on the energy entropy signal, and selecting and combining two or more of the plurality of statistical features, wherein the statistical features include two or more of the following:
Shannon entropy of power spectral density (PSD) of energy entropy;
minimum envelopes of x-, y-, and z-axis signals;
minimum Shannon entropy of PSD of x-, y-, and z-axis entropies;
standard deviation of interbeat intervals (IBIs);
differences of median filtered IBIs;
determinism of recurrence plot of energy entropy;
Kurtosis of energy entropy;
minimum peak-to-peak amplitude of x-, y-, and z-axis signals;
peak-to-peak amplitude of energy entropy;
laminarity of recurrence plot of energy entropy;
Shannon entropy of horizontal structures in recurrence plot of energy entropy;
standard deviation of time-averaged spectrogram;
minimum standard deviation of peak positions in spectrogram; and
minimum standard deviation of peak widths in spectrogram.

15. The non-transitory computer medium of claim 14, wherein the physiological signals are ballistocardiogram (BCG) signals.

16. The non-transitory computer medium of claim 15, wherein the pre-processing module filters out signals due to motion, wherein the BCG signals are divided into a plurality of epochs, and an epoch of the epochs is classified as motion if a mean entropy $\overline{w}$ of an epoch is more than three scaled-median above deviations (cMAD) away from the median.

17. The non-transitory computer medium of claim 14, wherein the Shannon entropy of PSD of energy entropy is $$Entropy_i = -\sum_f prob_{f,i} \cdot \log(prob_{f,i})$$

wherein $prob_{f,i}$ is defined as one of the two following:

$$Prob_{f,1} = \frac{P_w(f)^2}{\sum_{f=0.5Hz}^{3Hz}(P_w(f))^2} \text{ and}$$

$$Prob_{f,2} = \frac{P_w(f)^2}{\sum_{f=0}^{f_s/2}(P_w(f))^2},$$

wherein f is limited to 0.5 Hz≤f≤3 Hz.

18. The method of claim 14, wherein the recurrence plot is expressed as:
$$R(i,j)=\Theta(\epsilon-\|s(i)-s(j)\|), s \in R^M, i,j=1,\ldots,N,$$
wherein N is the length of signal, $\epsilon$ is a threshold parameter and $\Theta(\cdot)$ is the Heaviside function.

19. The method of claim 14, wherein the spectrogram is generated by applying Short-time Fourier Transform to the energy entropy signal.

20. The method of claim 14, wherein the selecting of two or more statistical features comprises at least one of the following:
neighborhood component analysis (NCA);
principle component analysis (PCA);
denoising autoencoder in a neural network using raw feature inputs with noise corruption or missing components as autoencoder inputs;
a recurrent neural network; and
a convolutional neural network with deep neural network.

* * * * *